(12) United States Patent
Ross (10) Patent No.: US 8,954,354 B2
(45) Date of Patent: Feb. 10, 2015

(54) AUTOMATED INTRAVENOUS FLUID CONTAINER DELIVERY DEVICE AND SYSTEM

(75) Inventor: Graham Ross, Poway, CA (US)

(73) Assignee: CareFusion 303, Inc., San Diego, CA (US)

( * ) Notice: Subject to any disclaimer, the term of this patent is extended or adjusted under 35 U.S.C. 154(b) by 1383 days.

(21) Appl. No.: 12/106,071

(22) Filed: Apr. 18, 2008

(65) Prior Publication Data

US 2008/0275590 A1 Nov. 6, 2008

Related U.S. Application Data

(63) Continuation-in-part of application No. 11/969,044, filed on Jan. 3, 2008, now Pat. No. 8,257,337.

(60) Provisional application No. 60/915,627, filed on May 2, 2007.

(51) Int. Cl.
G06Q 30/00 (2012.01)
B65G 67/00 (2006.01)
A61M 5/148 (2006.01)
A61M 5/168 (2006.01)

(52) U.S. Cl.
CPC ......... *A61M 5/1483* (2013.01); *A61M 5/16827* (2013.01); *A61M 2205/3576* (2013.01); *A61M 2205/50* (2013.01); *A61M 2205/6072* (2013.01)
USPC ............................ 705/332; 414/373; 414/809

(58) Field of Classification Search
USPC ................................... 705/332; 414/373, 809
See application file for complete search history.

(56) References Cited

U.S. PATENT DOCUMENTS

| | | | |
|---|---|---|---|
| 4,559,036 A | * | 12/1985 | Wunsch ........................ 604/81 |
| 5,078,683 A | | 1/1992 | Sancoff et al. |
| 5,090,963 A | | 2/1992 | Gross et al. |
| 5,314,243 A | * | 5/1994 | McDonald et al. ........... 312/215 |
| 5,317,506 A | | 5/1994 | Coutre et al. |

(Continued)

FOREIGN PATENT DOCUMENTS

| | | |
|---|---|---|
| JP | 2003225305 | 8/2003 |
| JP | 2006034845 | 2/2006 |

OTHER PUBLICATIONS

"Robot Delivers Medications at University of Maryland Shock Trauma Center", May 10, 2004, available at: http://www.umm.edu/news/releases/robot.htm.*

*Primary Examiner* — Kevin Flynn
(74) *Attorney, Agent, or Firm* — McDermott Will & Emery LLP (57) ABSTRACT

An IV product transport device is configured to transport an IV product from one location to another in automated fashion. The transport device may comprise a chassis with one or more ports for IV products. A drive mechanism is configured to move the transport device. In one embodiment, the transport device includes a controller. Information may be provided to the controller about an IV product, such as its intended destination or use. The controller may also exchange information with a delivery device, such as an infusion pump, to verify that the IV product is delivered to the proper destination. The transport device may include a delivery mechanism for off-loading an IV product. The transport device may deliver IV products of various configurations, including one in which the product comprises a flexible bag and a container housing for supporting and protecting the fluid bag.

16 Claims, 7 Drawing Sheets

(56) References Cited

U.S. PATENT DOCUMENTS

| | | | |
|---|---|---|---|
| 5,873,731 A | 2/1999 | Prendergast | |
| 5,896,297 A * | 4/1999 | Valerino, Sr. | 700/213 |
| 6,000,486 A * | 12/1999 | Romick et al. | 180/23 |
| 7,236,936 B2 | 6/2007 | White et al. | |
| 2002/0038392 A1 * | 3/2002 | De La Huerga | 710/8 |
| 2002/0158058 A1 * | 10/2002 | Faries et al. | 219/400 |
| 2003/0077156 A1 * | 4/2003 | Bingman | 414/409 |
| 2003/0140929 A1 * | 7/2003 | Wilkes et al. | 128/898 |
| 2003/0165373 A1 * | 9/2003 | Felder et al. | 414/331.07 |
| 2004/0051368 A1 | 3/2004 | Caputo et al. | |
| 2004/0073177 A1 | 4/2004 | Hickle | |
| 2005/0108057 A1 * | 5/2005 | Cohen et al. | 705/3 |
| 2005/0209547 A1 | 9/2005 | Burbank et al. | |
| 2006/0125356 A1 * | 6/2006 | Meek et al. | 312/215 |
| 2006/0178619 A1 | 8/2006 | Simpkins | |
| 2006/0265186 A1 | 11/2006 | Holland et al. | |
| 2008/0199298 A1 * | 8/2008 | Chilson et al. | 414/809 |

* cited by examiner

FIG. 13

AUTOMATED INTRAVENOUS FLUID CONTAINER DELIVERY DEVICE AND SYSTEM

RELATED APPLICATION DATA

This application is a continuation-in-part of U.S. application Ser. No. 11/969044, filed Jan. 3, 2008, and claims priority to U.S. Provisional Application Ser. No. 60/915627, filed May 2, 2007.

FIELD OF THE INVENTION

The present invention relates to intravenous fluid containers and, more particularly, a system and device for delivering those containers.

BACKGROUND OF THE INVENTION

In the United States, most intravenous fluids are contained in rectangular flexible bags, commonly referred to as intravenous or "IV" bags. These bags are equipped with multiple septums or other fluid connections that allow additional fluids to be added to the bag or which permit connection of the bag to a tube that feeds the fluid to the patient. The bags are floppy and subject to puncture if they come into contact with sharp items. Alternate containers, which may be more prevalent in other countries, include glass bottles and soft plastic bottles.

Figure 1:
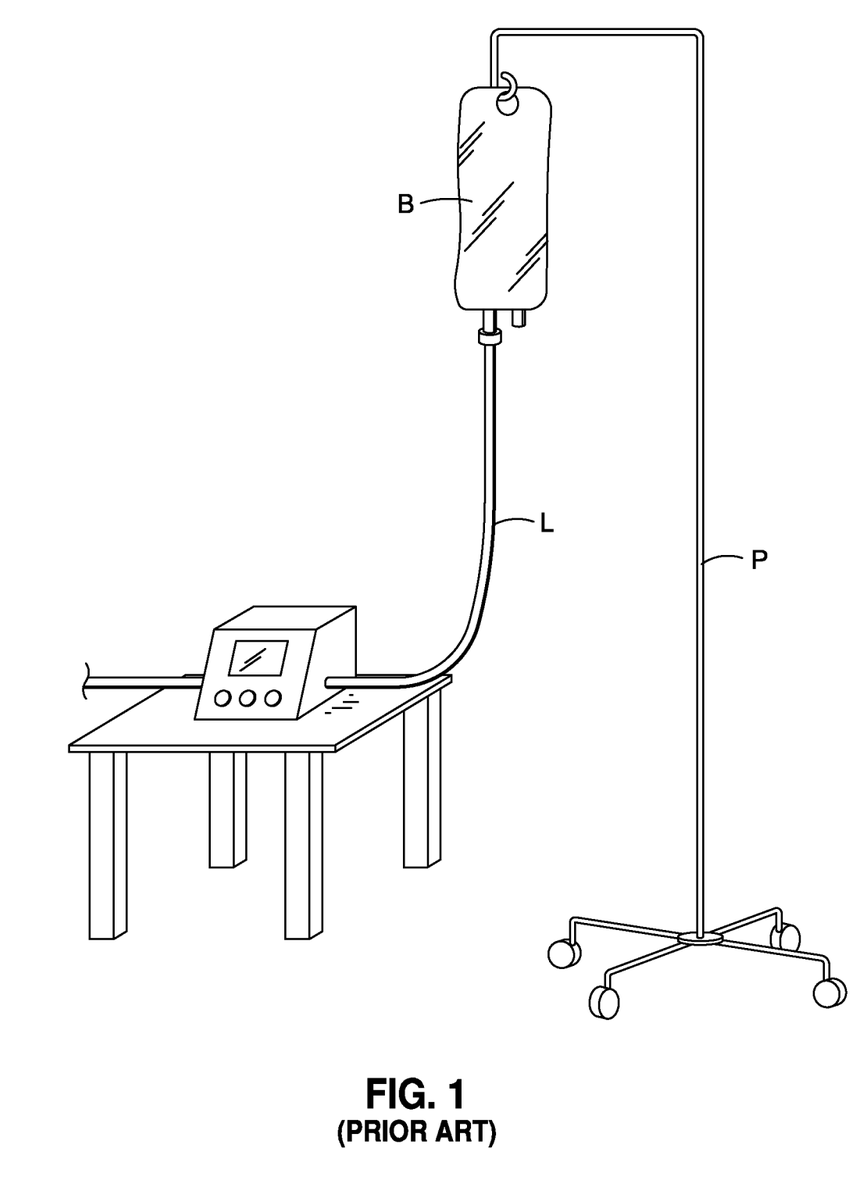
FIG. 1 illustrates an IV bag and delivery method in accordance with the prior art.

Administration of these IV fluids, regardless of the container, requires that the fluid container be suspended at some height, typically 0.5-1.0 meter, above the patient or an infusion pump. This container is then connected by a flexible tube to either the patient directly or to the infusion pump. Mounting the fluid container above the delivery point generates a positive pressure due to gravity at the connection of the infusion tube to the patient or pump. One embodiment of such a mounting is illustrated in FIG. 1, wherein an IV bag B is mounted in an elevated position on a pole P. A fluid delivery line L leads from the bag B.

Every step of the processing of such a fluid container has associated risks to the patient, primarily due to the completely manual process of utilizing the container. For example, the IV bag may be incorrectly labeled when additional drugs are added in the pharmacy or other location, leading to a risk that the IV fluid will be administered to the incorrect patient. The bag may also be dropped or mishandled in transit due to the floppy design of the container, leading to either leakage or contamination of the contents or external connections. The current method of providing IV fluids is also entirely manual, requiring labor to prepare, transport and connect the IV bag.

SUMMARY OF THE INVENTION

Various aspects of the invention comprise IV products and methods of utilizing such products.

In one embodiment, a device and system are provided for delivering IV products. One aspect of the invention is a transport device having a chassis and one or more IV product ports. The ports are configured to accept one or more IV products.

Preferably, the transport device is movable. The chassis may be mounted upon one or more wheels. A propulsion or drive may be configured to drive one or more of the wheels.

The transport device may include a control, such as a controller. In one embodiment, information may be provided to and transmitted from the transport device via a communication link and/or other information reading or transmitting devices. For example, the transport device may include a wired or wireless communication link over which information may be exchanged, such as to or from a computer or computing network. The transport device might also include information reading devices such as a bar code reader.

The transport device may be configured to transport or move one or more IV products from a first location to a second location. The transport device may also be configured to deliver or unload the IV products. For example, a delivery mechanism may be configured to expel and IV product from its port on the transport device to a destination device.

In use, an IV product may be loaded to the transport device at a first location. This location might be, for example, a pharmacy of a hospital. The IV product may be loaded into one of the IV product ports of the transport device. In one embodiment, information may be provided to the transport device at that time. For example, information regarding the designated delivery location, intended patient, IV product content or other information may be provided to the transport device.

The transport device may then transport the IV product from the first location to the second location or destination. In one embodiment, the transport occurs autonomously, with the transport device self-propelling itself to the designated location.

At the designated location, the transport device may interrogate a destination device. This interrogation may be used to confirm that the IV product is reaching the intended destination. In addition, the transport device may provide the destination device with information regarding the IV product.

Upon confirmation, the transport device may then deliver the IV product to the destination device. Such might comprise the transport device expelling the IV product there from to a pot of the destination device. The destination device might comprise, for example, an infusion pump.

The transport device may be configured to deliver a wide range of IV products. In one embodiment, the IV product may comprise a fluid bag and a container housing. The fluid bag may comprise a flexible member for containing fluid. The fluid bag has at least one fluid connector to permit fluid to be transferred to and from the fluid bag. In one embodiment, the fluid connector may comprise a pierceable septum or other connector to permit a fluid connection to be established.

The container housing preferably comprises a rigid member for protecting and supporting the fluid bag. In one embodiment, the fluid bag and container housing may be separable, while in others they may be integrated. The container housing may completely enclose the fluid bag or only partially enclose the fluid bag, as in the case of a supporting frame.

The IV product may bear one or more information elements. The IV product may include mechanism for expelling fluid there from. The IV product may include additional features such as alignment members or elements for mating with external devices such as pumps, docking stations or the like.

Further objects, features, and advantages of the present invention over the prior art will become apparent from the detailed description of the drawings which follows, when considered with the attached figures.

DETAILED DESCRIPTION OF THE INVENTION

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

One embodiment of the invention is a device for delivering or transporting and IV container or product from a first location to a second location. Additional aspects of the invention comprise a system for providing an IV container at a first location, transporting the IV container from the first to a second location and then transferring the IV container for use.

Figure 2:
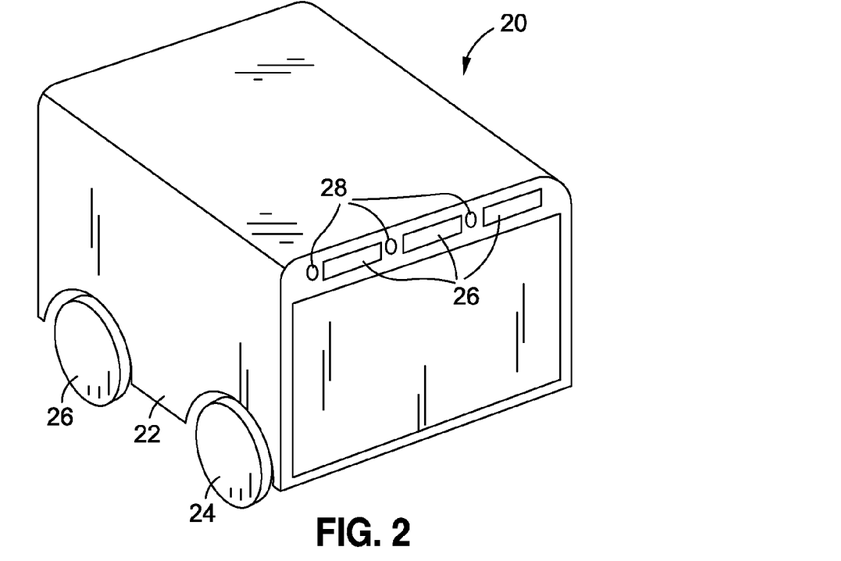
FIG. 2 illustrates and IV product delivery device in accordance with an embodiment of the invention.

FIG. 2 illustrates one embodiment of an IV container delivery or transport device 20. In a preferred embodiment, the delivery device 20 is self-propelled and configured to transfer an IV container from itself to another device.

In one embodiment, as illustrated, the transport device 20 comprises a housing or chassis 22. Preferably, the chassis 22 comprises a supporting structure or framework. In general, the chassis 22 may have a variety of configurations, including various shapes and having various constructions. The chassis 22 may be open or closed, such as comprising an open frame or a frame supporting one or more panels or the like, thus generally enclosing the device 20.

In one embodiment, the transport device 20 is movably supported. As illustrated, the chassis 22 may be supported by a pair of front wheels 24 and a pair of rear wheels 26. These wheels may be mounted on axles or other supporting structures connected to or forming a part of the chassis 22. Of course, the transport device 20 may be supported in other fashions, such as with a greater or lesser numbers of wheels (such as only one front wheel and two rear wheels, one rear wheel and two front wheels, more than four wheels) and/or with other types of supports, such as tracks, skids, balls, or the like.

In a preferred embodiment, as detailed above, the transport device 20 is self-propelled, meaning that at least one mechanism is provided with the transport device 20 for moving the device. Such a mechanism may comprise a drive or propulsion device or system. In other embodiments, the transport device 20 could be configured to be externally propelled, such as by connecting the transport device 20 to another propelled device, by mounting the transport device 20 on a track including a connection to a moving element or the like.

In one embodiment, the transport device 20 is configured to support one or more IV containers. The IV containers may be housed in an interior portion of the transport device 20 or externally thereto. In one embodiment, the transport device 20 defines one or more ports 26 for housing IV containers. In one embodiment, the ports 26 are defined by the chassis or components thereof. In other embodiments, the ports 26 might comprise devices (such as small housings) which are associated with the chassis. These ports 26 may be configured to at least partially enclose an IV container. In one embodiment, the ports 26 may be configured to entirely enclose an IV container, so as to protect the IV container from tampering or the like. For example, the ports 26 may define an internal or interior area in which an IV container may be located. In one embodiment, each port 26 may include a door which may be opened and closed and through which the IV container(s) may be loaded. The door(s) may lock when an IV container is loaded (such as controlled by a controller of the transport device (20), as detailed below).

Figure 12A:
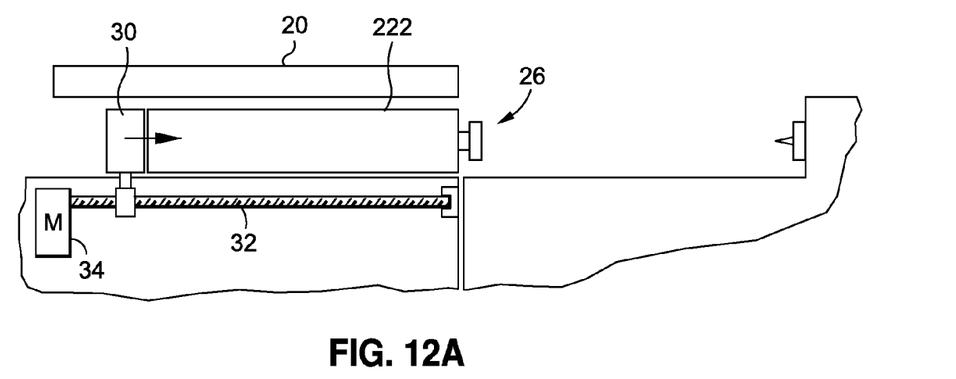
FIGS. 12A and 12B illustrate a method of transferring an IV product from a delivery device to a docking station.
Figure 12B:
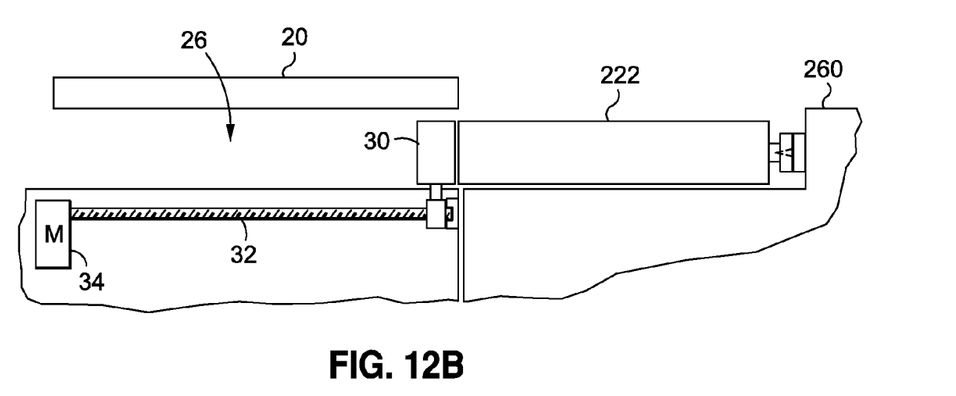

The transport device 20 may be configured to deliver one or more IV or fluid containers or products from the device 20 to another device or location. In one embodiment, the transport device 20 thus includes one or more delivery mechanisms for moving the IV containers from the ports 26. One example of such a mechanism is illustrated in FIGS. 12A and 12B and will be described in greater detail below.

The transport device 20 may be configured to receive information from or provide information to another device. In this regard, the transport device 20 may include one or more information readers, such as barcode canners 28, and/or one or more data or communication ports or interfaces.

Figure 3:
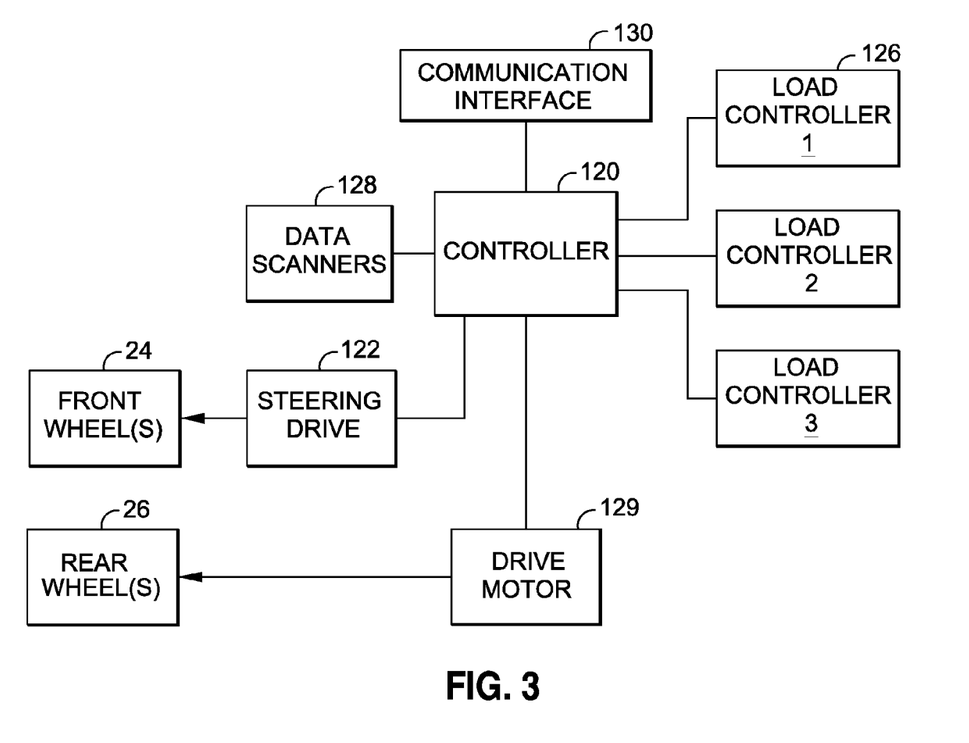
FIG. 3 is a schematic diagram of a control system of the delivery device illustrated in FIG. 2.

FIG. 3 schematically illustrates one configuration of a transport device 20. As illustrated, the transport device 20 may have one or more controllers 120. While the transport device 120 might have a single master controller, it might instead have main controller and a plurality of sub-controllers. The controller 120 might be, for example, a computing-type device having a micro-processor with associated memory and configured to execute machine readable instructions or software. The controller 120 might, however, comprise a range of hardware and/or software.

In one embodiment, the controller 120 is configured to transmit control instructions or signals to effect movement of the transport device 20. For example, the controller 120 may be configured to transmit signals to a steering motor 122 to effect turning of the front wheels 24. The controller 120 may also be configured to transmit signals to a drive motor 129 (or other propulsion device) to effect rotation of the rear wheels 26 in a forward or reverse direction.

In one embodiment, the controller 120 may transmit signals to one or more load controllers 126. The load controllers 126 may be configured to effect delivery of one or more of IV containers from the transport device 20. The load controllers 126 may comprise, for example, motors driving screws that cause a stop to press an IV container from its port, as further detailed below.

As indicated, the controller 120 may be configured to interface with one or more information reading devices or data scanners 128. Such devices may comprise bar code readers, smart card readers, magnetic stripe readers, comprise an RF detector or be other types of devices now known or later developed. The controller 120 may also include or be connected to one or more communication interfaces or ports 130 for receiving and/or transmitting information. For example, control instructions may be provided to the controller 120 via the communication interface 130, such as from a remote computer. In one embodiment, the communication interface 130 may be configured to transmit or receive information over a wired or wireless communication link.

Of course, the transport device 20 may include a plurality of other features. For example, though not illustrated, the transport device 20 preferably includes a power source. The power source might comprise one or more rechargeable batteries. The various components of the transport device 20 may be powered via one or more connections to the power source. The transport device 20 might also include various user inputs, such as a touch-screen, buttons or the like. Such inputs may be utilized by a user to obtain information from the transport device 20 (such as current battery status, current load or delivery instructions) or be used to program or provide instructions to the transport device. The displays may be utilized to display information, such as the current status of the transport device.

In one embodiment, the transport device 20 is configured to support, transport and deliver one or more fluid containers, and preferably one or more IV containers. The configurations of such containers may vary. For example, the IV product might comprise a flexible bag or a rigid container or bottle. In a preferred embodiment, however, the IV container comprises an IV product comprising a housing and an associated IV bag or container. This container housing is preferably configured as a rigid support and protection structure for a flexible fluid bag. In one embodiment, the container housing includes a mechanism for expelling fluid from the bag contained therein.

Figure 4:
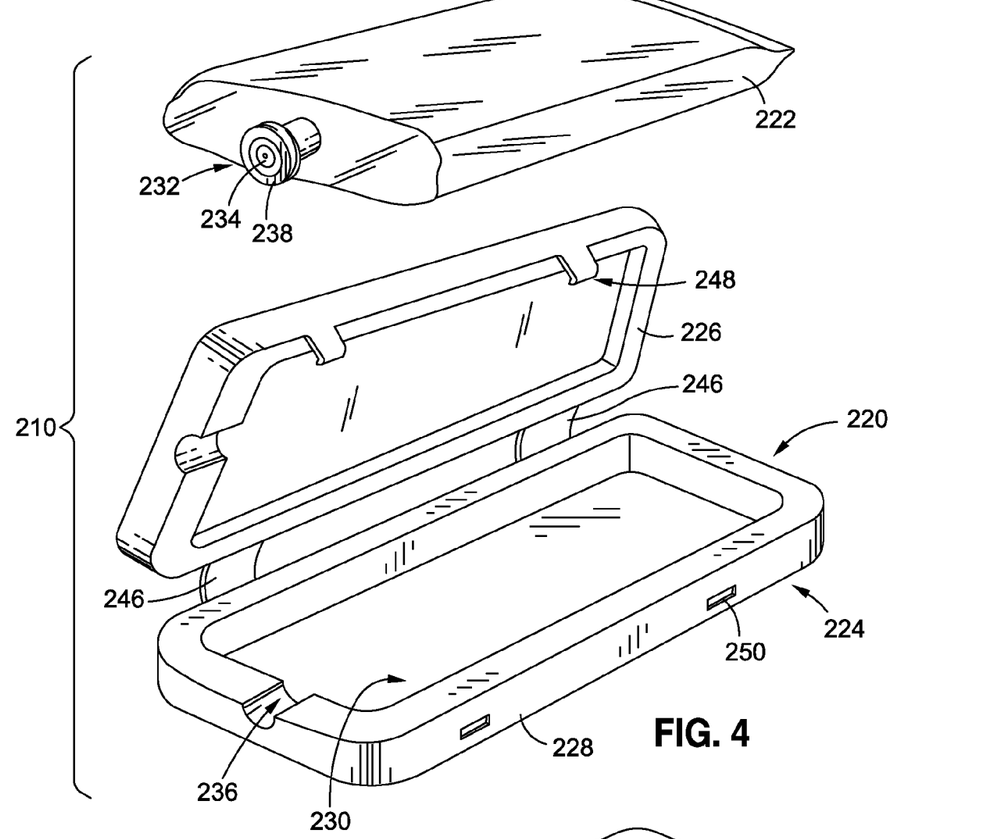
FIG. 4 illustrates an IV product in accordance with an embodiment of the invention, the product shown in an open/unassembled state.

As illustrated in FIG. 4, in one embodiment an IV product 210 comprises a container housing 220 and a fluid bag or container 222. The container housing 220 may have a variety of shapes, sizes and configurations. In general, the container housing 220 is configured to support the fluid or IV bag 222. In one embodiment, as illustrated, the container housing 220 may generally house the fluid bag 222. As detailed below, the container housing 220 may be a relatively rigid structure which not only supports but also protects the fluid bag 222.

The fluid bag 222 preferably comprises a relatively flexible container for fluid, such as medication or the like. The fluid bag 222 may thus have a relatively thin wall construction.

Figure 5:
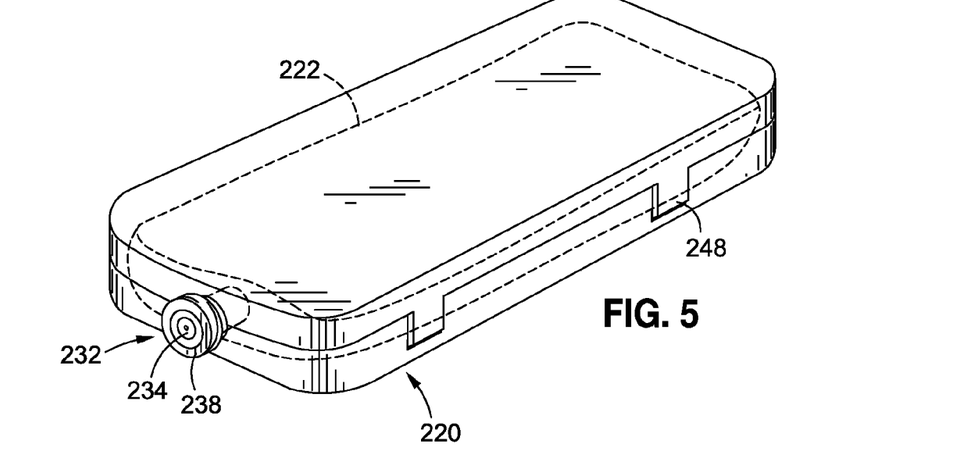
FIG. 5 illustrates the IV product in FIG. 4 in a closed/assembled state.

In one embodiment, as illustrated in FIGS. 4 and 5, the container housing 220 is configured as a body 224 defining an interior area for accepting, housing or containing the IV bag 222 therein. The body 224 may be constructed from a variety of materials and have a variety of shapes. In one embodiment, the body 224 has a top portion 226 and a bottom portion 228. The top and bottom portions 226,228 each have an exterior surface and an interior surface. The interior surfaces may define concavities such that when the top and bottom portions 226,228 are connected, the body 224 defines an interior area 230.

In one embodiment, as illustrated, the container housing 220 is generally rectangular in shape for accepting a correspondingly shaped fluid bag 222. It will be appreciated, however, that the container housing 220 (and fluid bag 222) might have a variety of other shapes (such as square, round, etc.).

The top and bottom portions 226,228 may be movable relative to one another to provide access to the interior area 230. For example, as illustrated in FIGS. 2, the top and bottom portions 226,228 may be hingedly connected, thus permitting the top portion 226 to rotate from an open position to a closed position relative to the bottom portion 228. Of course, the top and bottom portions 226,228 might be moved between "open" and "closed" positions in other fashions, such as by having the top and bottom portions connectable in other fashions. In other embodiments, a portion of either the top and/or bottom may be openable or closeable. For example, the top portion 226 might have a door therein which can be opened to provide access to the interior area 230 of the container housing 220.

The container housing 220 might have other configurations. For example, the container housing 220 might be a relatively open structure, such as a webbed structure, or have a solid bottom portion but relatively open top portion.

The container housing 220 may be constructed of a variety of materials. For example, the container housing 220 might be molded from plastic or resin materials. The container housing 220 might be configured so that all or part thereof is transparent or opaque. The container housing 220 might be configured to be transparent, for example, to permit the fluid bag 222 therein to be easily viewed.

In one embodiment, the container housing 220 and fluid bag 222 are configured to provide a fluid connection. As illustrated in FIGS. 4 and 5, the fluid bag 222 is provided with at least one fluid connector 232. In one embodiment, this connector 232 comprises an extension of the body of the fluid bag 222 or a conduit or fluid path in communication therewith. The connector 232 may include a sealable fluid access, such as a no-drip needle-less connector. Such elements are well know in the art and may comprise a pierceable septum 234.

In one embodiment, the connector 232 may comprise a generally tubular member extending from the body of the fluid bag 222. The connector 232, or at least a portion thereof, may be relatively rigid. For example, a distal or end portion thereof may be relatively rigid while the proximal portion of the connector 232 at its connection to the fluid bag 222, may be flexible.

Preferably, the container housing 220 includes a fluid connector support. In one embodiment, the support 234 comprises a portion of the top and bottom portions 226,228 of the container housing 220. In one embodiment, the support 234 may be configured as an aperture 236 for accepting therein a portion of the fluid connector 232 of the fluid bag 222.

Preferably, the support 236 is configured to selectively capture and maintain the fluid connector 232 in a fixed position, such as for mating of the fluid bag 222 with a mating fluid connector or fluid delivery line, as detailed below. In one embodiment, to capture the fluid connector 232 and to prevent the fluid connector from sliding back into the interior 230 of the container housing 220, a flange 238 or other outwardly extending element may be provided on the fluid connector 232. The flange 238 is preferably sized to prevent the fluid connector 232 from moving backwardly through the support 236, as best illustrated in FIG. 5.

The support 236 may thus have a variety of configurations and features. For example, the support 236 might simply be an opening in the top or bottom portion 226,228 of the container housing 220 through which the fluid connector 232 may extend. In other embodiments, the support 236 might comprise a clip or other element for selectively engaging the fluid connector 232.

In one embodiment, the IV product 210 may include a means or mechanism configured to expel or deliver the contents of the fluid bag 222. In one embodiment, such a mechanism is configured to create a force or positive pressure upon the fluid bag 222, thus tending to force fluid from the fluid bag 222. As detailed, one embodiment of such a mechanism may be configured to reduce the volume of the interior space 230 within the container housing 220, thus reducing the space which may be occupied by the fluid bag 222.

Figure 6A:
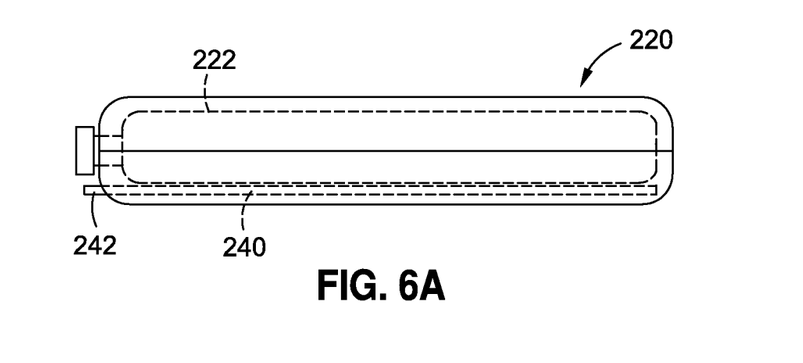
FIG. 6A illustrates another embodiment of an IV product in accordance with the invention, the product in a first condition.
Figure 6B:
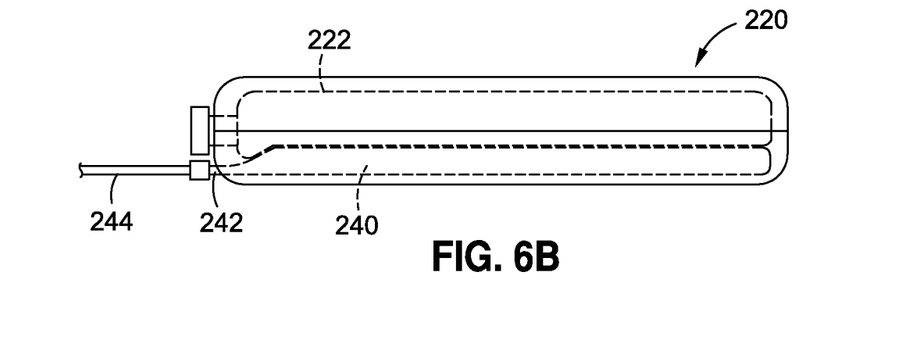
FIG. 6B illustrates the IV product in FIG. 6A in a second condition.

One embodiment of such an expelling mechanism is illustrated in FIGS. 6A and 6B. In a preferred embodiment, the mechanism comprises a member or members having a changeable size or volume. For example, as detailed below, in one embodiment, the mechanism may comprise a bellows 240 comprising a bag or body having a changeable volume. In one embodiment, the volume may be changed by changing a volume of fluid (such as air or liquid) within the bellows 240. In another embodiment, the mechanism may comprise one or more mechanical devices, such as a spring-driven body.

Referring to FIGS. 6A and 6B, the bellows 240 may comprise a bag which is located in the container housing 220. The bellows 240 preferably has an inlet 242 through which fluid may pass into and out of the bellows 240. In one embodiment, the container housing 220 may thus include an opening from the interior to the exterior thereof to provide access to the inlet 242 of the bellows 240.

In one embodiment, the bellows 240 may comprise a flexible bag, such as a rubber or plastic bag. A fluid delivery device, such as an air pump or the like, may be connected to the inlet 242 of the bellows 240, such as via an air line 244, thus providing fluid thereto. As will be appreciated, when fluid is delivered to the bellows 240, the fluid causes the bellows 240 to expand, as best illustrated in FIG. 6B. The bellows 40, in turn, compresses the fluid bag 222 in the container housing 220, tending to force fluid from the fluid bag 222 (when an appropriate fluid connection is provided to the fluid connector 232 of the fluid bag 222).

Of course, the expelling mechanism may have a variety of other configurations. For example, the bellows might be configured to be filled with liquid or air and liquid. In other embodiments, more than one bellows might be provided. In the embodiment illustrated, the bellows 240 is located below the fluid bag 222. However, the bellows 240 might be located above and/or below the fluid bag 222, or might be located at one or both ends of the fluid bag 222. Also, more than one bellows 240 might be provided.

As indicated, other types of mechanisms might be provided for expelling fluid from the fluid bag 222. For example, the mechanism might comprise a movable platform located in the interior 230 of the container housing 220. The mechanism might include a biasing member, such as one or more springs, for moving the platform inwardly to compress the fluid bag 222.

In order to maintain the container housing 220 in a closed position, such as when the expelling mechanism is activated and a force is being generated in the interior 230 thereof, the top and bottom portions 226,228 may be secured to one another. As illustrated in FIGS. 4 and 5, the top and bottom portions 226,228 may be connected by one or more elements 246, such as hinges, at one portion or side thereof. In one embodiment, the hinges 246 may comprise flexible portions of material which are connected to both the top and bottom portions 226,228 of the container housing 220. In other embodiments, the hinges 246 might comprise two or more members which are configured to move relative to one another, one of which is connected to the top portion 226 and the other of which is connected to the bottom portion 228 of the container housing 220.

One or more latches 248 may be provided for connecting opposing or other portions of the container housing 220. In one embodiment, each latch 248 be associated with the top portion 226 of the container housing 220 and be configured to selectively engage the bottom portion 28 of the container housing 220.

In the illustrated embodiment, each latch 248 is movably or hingedly connected to the top portion 226 of the container housing 220. The latch 248 has a tab (not visible) for selective engagement with the bottom portion 228 of the container housing 220, such as a slot or notch 250 therein. When engaged, each latch 248 pulls the top portion 226 and bottom portion 228 towards one another.

In one embodiment, there may be more than one latch 248, such as two or more. Also, the latch 248 or other securing mechanism may have other configurations. For example, the latch might comprise a rotating catch, might include one or more threaded members or the like.

In one embodiment, the top and bottom portions 226,228 of the container housing 220 may be sealable so as to provide a sealed interior space 230. In such a configuration, air or other fluid might be input directly into the interior of the container housing 220. As the pressure of this fluid increases, the fluid bag 222 is compressed, expelling the contents of the bag 222. In other embodiments, it is possible to inject air directly into the fluid bag 222 in order to force the fluid therefrom, or force air or other fluid into a chamber or bellows formed with or in the fluid bag 222.

Figure 7:
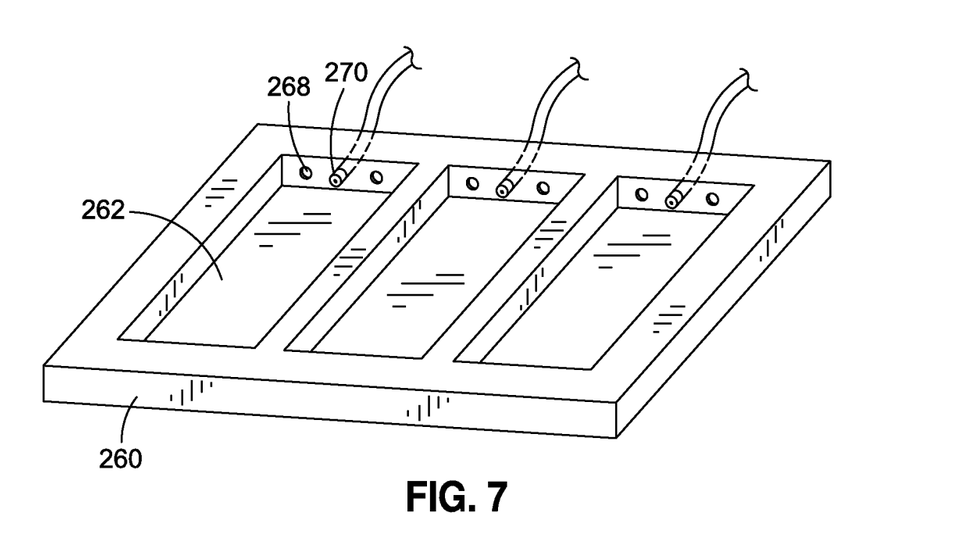
FIG. 7 illustrates a docking station or receptacle for an IV product.

In one embodiment of the invention, as illustrated in FIG. 7, the IV product of the invention may be configured to engage a docking station or receptacle 260 or otherwise be connected to one or more other devices or elements. For example, in one embodiment, a docking station 260 may comprise or define one or more ports 262 for one or more corresponding IV products. The ports 262 might comprise recessed areas in a body or structure, into which a container housing may be located. In other embodiments, the ports may simply comprise fluid connectors or connections for mating connection to the fluid connector 232 of the fluid bag 222. There may be as few as one, or two or more ports 262 associated with the docking station 260.

In one embodiment, one or more connectors or other members may be provided for mating the container housing 220 to a port 262 of the docking station 260 or another element. For example, referring to FIG. 8, the container housing 220 may include at least one element for mating engagement with the docking station 260 or an element thereof.

Figure 8:
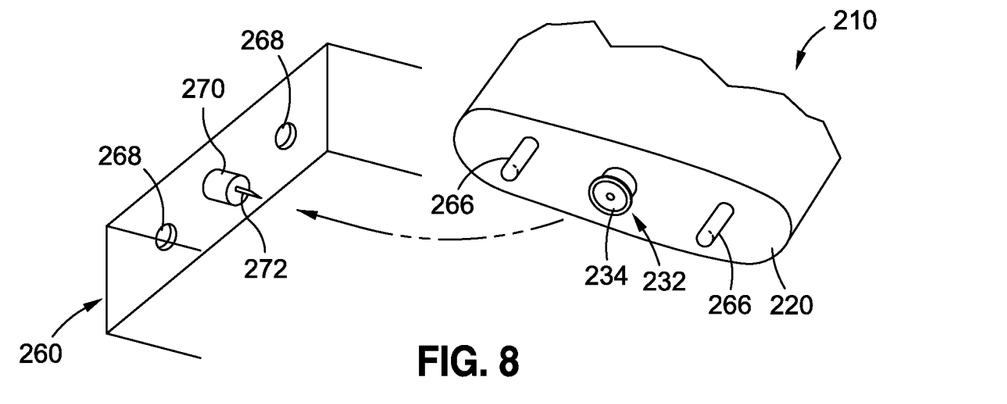
FIG. 8 illustrates a connector configuration for an IV product and docking station.

As illustrated, one or more pins 266 may extend outwardly from the container housing 220. In one embodiment, a pair of pins 266 may extend outwardly from an end of the container housing 220. These pins 266 may be configured to engage mating apertures 268 of the docking station 260.

In one embodiment, when the container housing 220 and associated fluid bag 222 are connected to the docking station 260, a fluid connection is preferably provided to the fluid bag 22. As illustrated, a mating fluid connector 270 is preferably provided at each port 262 for mating with the fluid connector 232 of the fluid bag 222.

In an embodiment where the fluid connector 232 of the fluid bag 222 comprises a pierceable septum, the port fluid connector 270 may comprise a needle 272 or similar piercing member. The needle 272 may be inset into the docking station 260 or a shroud or the like so as to prevent accidental needlesticks.

Preferably, the container housing 220 is moved into engagement with the docking station 260 at a port 262 thereof. The container housing 220 is aligned with the docking station 260, such as by extending the pins 266 into the mating apertures 268 in the docking station 260. As this occurs, a fluid connection is preferably established between the docking station 260 and the fluid bag 222, such as by the needle 272 piercing the septum 234 of the fluid bag 22.

Of course, a wide variety of other elements may be utilized to accomplish the purpose of aligning and/or connecting the connector housing 220/fluid bag 222 with the other member. For example, IV product might be aligned with a mating fluid connector as a result of the shape of the inset or port of the docking station, whereby the container housing 220 fits tightly within the inset or port. Other types of locking or connecting elements might be used in addition to or separately from such an alignment mechanism, such as the disclosed pin(s). Preferably, these elements include at least one member or element of the container housing 220 or associated with the container housing 220 for selectively engagement with an external component, such as a port, dock, pump or the like. In this regard, it will be appreciated that the container housing 220 and associated fluid bag 222 may be configured to engage other than a docking station 260. For example, the IV product of the invention could be configured to directly engage a fluid pump or the like.

As indicated above, in one embodiment, an expelling mechanism is provided to aid in expelling fluid from a fluid bag 222 associated with the container housing 220. In one embodiment, that mechanism may be associated with another device, such as the docking station 260 or port to which the IV product may be coupled. In one embodiment, when the container housing 220 is mated to a docking port, a fluid connection may be established with the fluid bag 222 and a fluid connection may be established with the interior 230 of the container housing 220 or with the bellows, thus allowing fluid to be introduced therein. In another embodiment, the external device may include means for compressing the fluid bag 222, such as a movable plate or the like.

Figure 9:
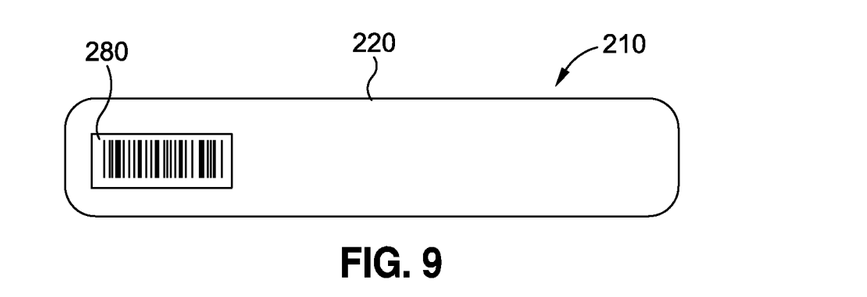
FIG. 9 illustrates an IV product of the invention bearing an information element.

As illustrated in FIG. 9, the IV product 210 may be provided with information, such as an information element 280. In a preferred embodiment, the information element 280 is associated with the container housing 220. The information element 280 may, however, be associated with the fluid bag 222. In such instance, the container housing 220 may be configured to allow the information element 280 to be visible, such as by having a port or window aligned therewith or having portion thereof be transparent so that the information element may be read through the container housing 220. The information element 280 may comprise printing, such as a 2 or 3-D bar code, text or symbols or combinations thereof. For example, in the embodiment illustrated in FIG. 9, the information element 280 comprises a printed bar code. The information element might 280 might also comprise an RFID tag, magnetic stripe, microchip (such as a chip located on the container, the chip having a connector for connection to a reader located at a docking station or other device), memory device or other electronic information storage device or the like.

The information element 280 may be configured to comprise or identify a variety of information. For example, the information element 280 may identify a file of information, or itself provide specific information. This information might identify, for example, the fluid which is located in the fluid bag 222, the patient for which the fluid is intended, the source of the fluid bag (such as manufacturer), expiration date, product size or volume, doctor, hospital, pharmacy, or a wide range of other information.

Figure 10:
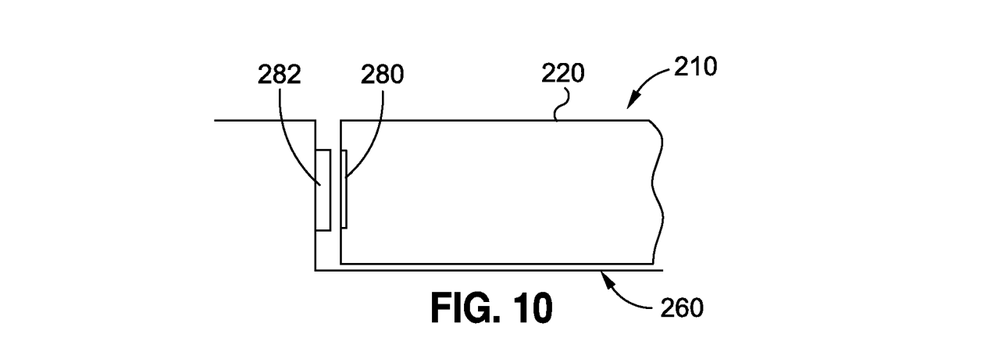
FIG. 10 illustrates an information reader for reading an IV product information element.

As illustrated in FIG. 10, a reader 282 may be provided for reading the information associated with the IV container, such as the information element 280. The reader 282 may comprise one or more of a variety of devices configured to read, capture or otherwise receive information. For example, the reader 282 might comprise an optical scanner for reading printed text, a bar code or the like. The reader 282 might comprise a magnetic stripe reader for reading magnetically encoded information.

In one embodiment, as illustrated in FIG. 10, the reader 282 may be associated with the docking station 260 or other IV product receptacle. Preferably, the reader 282 is situated or oriented to read the information associated with the IV container when the container 220 is associated with the docking station 260. Thus, in one configuration, a reader 282 is preferably associated with each of the ports 262 of the docking station 260. For example, a reader 282 may be provided at an end of each of the ports 262 for reading the information element 280 at the end of the container 220, as illustrated in FIG. 10.

Of course, a reader 280 may be associated with other elements or devices. For example, if the IV container is to be associated with an infusion pump, the reader could be associated directly with the pump.

Figure 11:
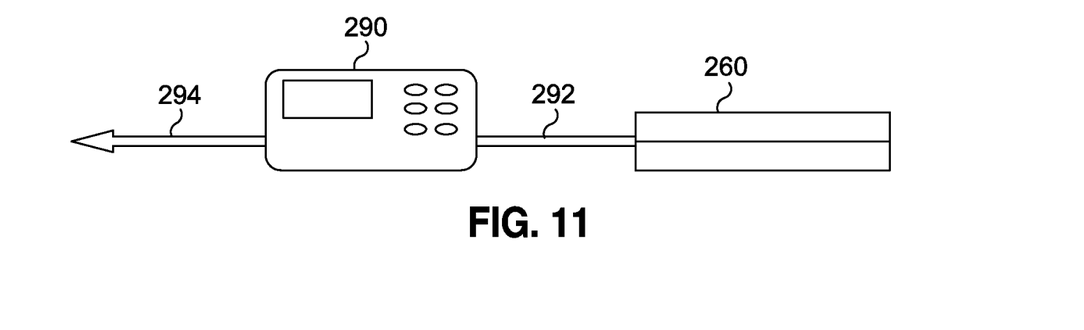
FIG. 11 illustrates a docking station coupled to an infusion pump for delivering fluid from an IV product of the invention.

As illustrated in FIG. 11, a docking station 260 may be associated with an infusion pump 290. As detailed above and illustrated in FIG. 7, the docking station 260 may be configured to receive one or more IV products. Preferably, when an IV product is associated with the docking station 260, a fluid connection is established with the IV product.

As illustrated, one or more fluid lines 292 may be provided between the docking station 60 or other receptacle and the infusion pump 290. The infusion pump 290 may be configured to deliver fluid to one or more delivery lines 294, such as a fluid line leading to a patient.

Additional aspects of the container transport device 20 will now be described. In one embodiment, as detailed, the transport device 20 is configured to transport one or more IV containers, such as the IV product just described. In one embodiment, the IV product may first be prepared, such as at a hospital pharmacy. This could comprise filling the fluid bag 222 with appropriate fluid (such as medication, saline, etc.). In an embodiment in which the fluid bag 222 and container housing 220 are separated or separable, the fluid bag 222 may then be associated with a container housing 220. For example, as indicated above, this may comprise opening the container housing 220 and inserting the fluid bag 222 therein.

In the embodiment illustrated in FIG. 4, the top portion 226 of the container housing 220 may be opened relative to the bottom portion 28, thereby providing access to the interior area 230. After the fluid bag 222 is inserted, the top portion 26 may be closed relative to the bottom portion 228 to trap or contain the fluid bag 222. In the embodiment illustrated, the latches 248 may be latched to secure the fluid bag 222 in the container housing 220. In an embodiment in which the fluid bag 222 and container housing 220 are integrated (such as being designed for a single use), the fluid bag 222 may be filled while associated with the container housing 20.

In order to secure the fluid bag 222 in position, the fluid connector 232 of the fluid bag 222 is preferably extended through the support 236. The flange 238 of the fluid connector 232 is located outside of the container housing 220.

Information is preferably associated with the IV product, such as the container housing 220. As indicated, the information may vary. For example, if the fluid bag 222 is prepared with particular medication for a particular patient, the information may include such. In one embodiment, such information may be input into a database and a printer may generate a barcode corresponding to the information. The barcode may, for example, be printed on an adhesive label which is affixed to the container housing 220.

The prepared IV product may be loaded to the transport device 20. Such may be accomplished manually or automatically. For example, relative to the embodiment in FIG. 2, an IV product may be loaded into one of the ports 26.

In one embodiment, information or instructions are provided to the transport device 20 regarding the IV product. This information may comprise information regarding the contents of the IV product, instructions for use of the IV product, patient information and/or information regarding the intended delivery location. This information might be transmitted to the transport device 20 via a communication link. For example, this information might be associated with a hospital pharmacy computer and be transmitted to the transport device 20, such as via the communication interface. In other embodiments, this information may be obtained from the IV product. For example, the information may be associated with the information element 280 of the IV product 210. The information element 280 might be read or scanned at the transport device 20 when the IV product 210 is loaded to the transport device (for example, each port might have a reader therein, the reader configured to read a barcode or other information element associated with the IV container or product). This information may be utilized by the controller of the transport device.

In one embodiment, the transport device 20 is configured to transport or deliver a fluid container, such as the above-described IV product 210, from a first location to at least one second location. For example, the transport device 20 may be configured to transport a prepared IV product from a hospital pharmacy to a patient's room. The transport device 20 may utilize delivery instructions in order to affect delivery. In this regard, the controller of the transport device 20 may cause the transport device 20 to move (such as by controlling the motors which effect driving and steering of the wheels). As is known in the art of moving vehicle control, the transport device 20 may be loaded with map information (such as hospital room layout) and/or may include various internal sensors (proximity sensors) or guides (external beacons or the like) to aid in navigation and/or guidance of the transport device 20.

Once the transport device 20 has arrived at a desired destination, the transport device may be configured to deliver the IV product or container to another device. One method of delivery will be described with reference to FIGS. 12A and 12B.

In one embodiment, as indicated above, the transport device 20 includes one or more load delivery mechanisms or devices. For example, as illustrated in FIG. 12A, each port 26 may include a load ram 30. The load ram 30 may be a body which is located behind a fluid container and movable from a first position towards a rear of the port 26 to a second position towards a front of the port 26. The load ram 30 might be, for example, mounted on a screw 32 which is rotatable by a motor 34.

In use, when the motor 34 is activated, the motor turns the screw 32, causing the load ram 30 to move. As illustrated, the load ram 30 may be moved forwardly to cause a fluid container 210 to be pressed outwardly from the port 26. Referring to FIG. 12B, the fluid container 210 may be delivered to a docking station 260.

Of course, a load delivery device may be associated with each port or only some of the ports. Other types of load delivery mechanisms might also be used. In general, such mechanisms are preferably configures to deliver an IV product from the transport device 20 another device or object. Other types of mechanism might include robotic arms, ports that tilt or move, among various others. For example, in one embodiment, the device might include an arm or element that is configured to engage the fluid container in a secure manner, thus permitting a fluid container to be "grabbed" for delivery to or from another location/device.

In one embodiment, before the transport device 20 delivers a fluid container to a secondary or destination device, the transport device 20 may be configured to confirm delivery. For example, when the transport device approaches a docking station or other destination device (infusion pump or the like), the transport device 20 may be configured to interrogate the secondary device, by either reading information (such as with the reader 28) from the device or by establishing a communication link therewith (wired or wireless) and exchanging information with the device. This may permit the transport device 20 to ensure that the fluid container is being delivered to the correct location.

The transport device 20 might also utilize information provided by the destination device for other purposes. For example, the transport device 20 might be configured to remove used fluid containers from the destination device. The docking station might indicate that a particular fluid container has been determined to be empty. The transport device 20 might then remove that fluid container from the destination device for disposal or return to another location.

Once delivered, the fluid container, such as the IV product 210, is preferably connected to a fluid delivery device. Of course, in one embodiment, the fluid container might simply be delivered and then installed or connected by another device or by a person. As illustrated in FIG. 12B, however, when the fluid container is delivered, such a connection may be automatically established. As illustrated, the fluid container my be associated with a receptacle or docking port so that a fluid connection is established with the fluid bag 222. For example, an IV product may be inserted so that the pins 266 fit within the corresponding apertures 268 of the port 266. When fully inserted, the needle 272 of the fluid connector 270 of the docking station 260 preferably penetrates a septum 32 of the fluid connector 232 of the fluid bag 222.

In one embodiment, the IV product may be located in a position at which gravity, an associated fluid pump or the like is sufficient to cause fluid to be delivered from the IV product. In other situations, such as where the IV product is at a level at which gravity or a fluid pump do not deliver fluid (or deliver it at sufficient rates), the fluid may be expelled from the bag by application of force. With reference to the embodiment illustrated in FIGS. 4A and 4B, air or other fluid may be delivered to the bellows 240, thus causing the bellows to expand, causing fluid to be expelled from the fluid bag 222. Of course, the method by which the fluid is expelled may vary depending upon the expelling mechanism, as detailed above.

Preferably, when the IV or other fluid product is utilized, the information associated therewith is read and that information is utilized. In the embodiment illustrated in FIG. 10, the information element 280 is read by the reader 282 when the container housing 20 is inserted into the port 262 of the docking station 260. In one embodiment, the reader 282 (and/or an external computing device) is configured to decode the information (such as the bar code) or to utilize the information to obtain information (for example, the information on the container housing 220 may identify a file or account containing information, such as located at a remote server).

The information may be utilized in the use of the IV product. For example, the information may be utilized by an infusion pump to control the flow rate of fluid to a patient. Referring to FIG. 9, for example, the reader may send control information from the docking station 260 to the infusion pump 290. The information might also be utilized to verify that the correct medication is being provided to a patient, that the fluid is intended for the particular patient, or a wide range of other purposes.

As indicated, the transport device may be configured to transport and/or deliver various types of fluid containers, including those other than the IV product described above. Such containers might contain various fluids, including medications. For example, while in various embodiments, the IV product was described as a container housing and fluid bag which are separable elements, in other embodiments, they may be inseparable. For example, the fluid bag may be formed with or securely connected to the housing. In the case where the container housing and fluid bag are separable, a used fluid bag might be discarded and the container housing re-used with a new fluid bag. In the case where they are inseparable, the entire unit may be discarded upon use.

The container housing may be generally enclosed or event sealed, or it might be an open frame or other support structure. The container housing may include additional features such as mounts or connections, such as to permit the container housing to be stored or picked up, such as with mechanical elements. For example, the container housing might include locating holes, slots, pins or the like for connection to a mounting rack or other structures or devices.

The fluid bag may be a single layer of material or may be multi-layer. The fluid bag may also be opaque, transparent, colored, conductive, non-conductive or have other properties.

As indicated, in one embodiment a mechanism may be provided for expelling fluid from the fluid bag. In one embodiment, the IV product may include a flow sensor and/or a volume sensor. The flow and/or volume sensor may provide feedback, such as to the expelling mechanism so as to provide a controlled fluid flow delivery rate from the fluid bag, and/or provide information regarding the amount of fluid delivered or amount of fluid remaining in the bag. For example, when the bag is nearly empty (as estimated by flow rate determination or directly by the volume sensor) a warning signal may be generated.

In one embodiment, container housings and docking ports or receptacles may have different configurations to permit only certain IV products to be mated with certain ports, receptacles or other devices. For example, the pattern of the pins extending from the container housing may vary, as may the corresponding aperture patterns of the ports. In this manner, for example, certain IV products might be usable only with certain ports, receptacles or other device. Such might be used to reduce the accidental connection of an IV product, and thus undesired delivery of fluid.

In one embodiment, when a fluid container is delivered by the transport device, the delivery information may be stored (such information might include a serial number or other identification of the secondary or destination device, time of delivery, etc.) and/or transmitted back to a remote location or central system.

Figure 13:
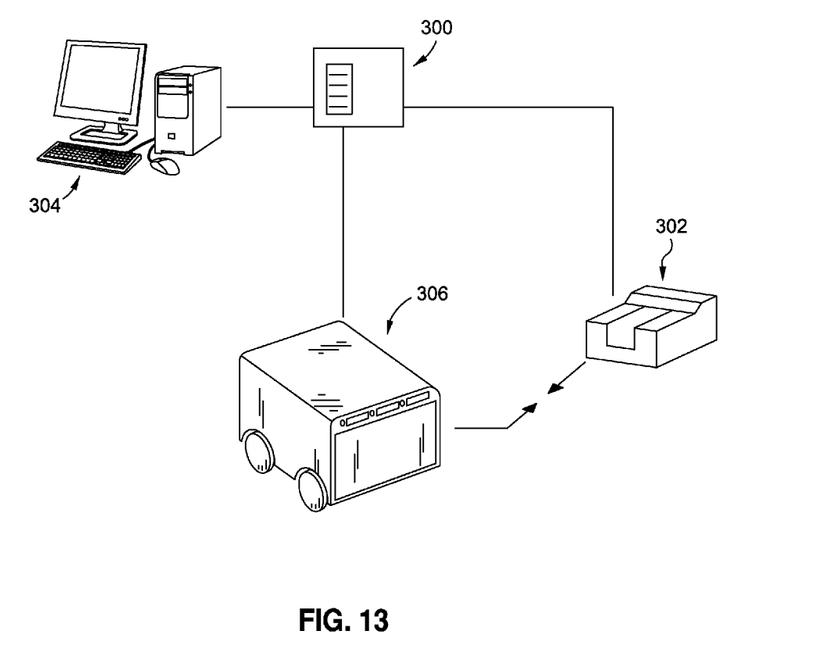
FIG. 13 illustrates one embodiment of a system of the invention.

One aspect of the invention is a system for delivering and using fluid containers. As illustrated in FIG. 13, the system may include one or more central computers or servers 300. Individual system elements, such as docking stations or receptacles 302, user terminals or computers 304, transport devices 306 and other device (infusion pumps, etc.) may communicate with one another and/or the central computer. The central computer 300 may, for example, store control instructions, data regarding fluid containers and their status (prepared, delivered, empty, etc.). The individual system elements may report to the central computer, thus automating the process of updating information regarding the containers.

As one aspect of the invention, information exchange between the various system elements may be utilized to reduce errors. For example, when a fluid container is prepared, instructions may be provided to the transport device (as indicated, such instructions might be provided directly from a computer or computing system, or be read from an associated IV or fluid product; these instructions may relate to the destination for the IV product(s) such as particular destination medical devices, hospital room, the uses for the products, patient identification, IV product content and use instructions). In addition, instructions may be provided to the destination device. When the transport device reaches the destination device, the transport device may interrogate the destination device (or vice versa) to ensure that the transport device has reached the correct destination device. In addition, when the fluid container is to be delivered, the secondary device may confirm that the correct container has been delivered (such as against information stored at or provided by a central computer, pharmacy computer or the like). This ensures that the correct medication, for example, has reached the correct destination. Further, instructions for use can be verified and those instructions can be used to automate use of the IV product (thus reducing human error associated with setting up the IV product for use).

The present invention has numerous advantages. In accordance with the invention, the delivery of a fluid container, such as an IV product, can be automated. In the medical setting, this can substantially reduce the labor needed to provided medications and the like to patients, lowering the cost of medical services. In addition, the automated procedure can be used to reduce the probability of error. In particular, the automated procedure can be used to reduce errors associated with human decision-making. In addition, the verification aspects of the automated procedure additional reduce the probability of error.

It will be understood that the above described arrangements of apparatus and the method there from are merely illustrative of applications of the principles of this invention and many other embodiments and modifications may be made without departing from the spirit and scope of the invention as defined in the claims.

What is claimed is:

1. An intravenous (IV) product delivery device comprising:
a movable chassis;
at least one drive coupled to the chassis and configured to move the chassis;
an IV product support coupled to the chassis and configured to support at least one IV product, the IV product comprising an IV product container and an IV fluid;
a powered delivery mechanism configured to move the at least one IV product container from the IV product support into a docking port of a fluid delivery device and establish a fluid connection between the IV product and the docking port such that the IV fluid from the IV product container is conducted through the docking port, wherein the fluid delivery device comprises an infusion pump; and
a controller coupled to the at least one drive and the powered delivery mechanism and configured to selectively cause the drive to move the IV product delivery device into proximity with the fluid delivery device based on patient delivery instructions received by the controller, and then to selectively cause the powered delivery mechanism to move the at least one IV product from the IV product delivery device into the docking port.

2. The IV product delivery device in accordance with claim 1, wherein the IV product support comprises a plurality of ports defined at least partially within the chassis and configured to receive an IV product therein.

3. The IV product delivery device in accordance with claim 1, wherein the delivery mechanism is configured to move an IV product outwardly of the IV product support and the transport device.

4. The IV product delivery device in accordance with claim 1, further comprising at least one information reader interfaced to the controller.

5. The IV product delivery device in accordance with claim 4, wherein the at least one information reader comprises a bar code scanner.

6. The IV product delivery device in accordance with claim 1, wherein the IV product comprises a container housing a flexible container therein.

7. A method comprising the steps of:
loading an IV product, comprising an IV product container and an IV fluid, onto a self-propelled IV product delivery device at a loading location;
transporting automatically by a drive mechanism of the IV product delivery device, based on patient delivery instructions received by the IV product delivery device, the IV product from the loading location to a fluid delivery device having a docking port that establishes a fluid connection with the IV product upon insertion of the IV product into the docking port, wherein the fluid delivery device comprises an infusion pump; and
transferring automatically by a powered delivery mechanism of the IV product delivery device said IV product container from the IV product delivery device into the docking port, thereby establishing the fluid connection between the IV product and the docking port such that the IV fluid from the IV product container is conducted through the docking port.

8. The method in accordance with claim 7, further comprising the step of transmitting information from a source to a controller of the IV product delivery device via a communication interface of the IV product delivery device.

9. The method in accordance with claim 8, wherein the transmitted information identifies an intended use for the IV product.

10. The method in accordance with claim 8, wherein the transmitted information is selected from the group consisting of: patient identification, intended destination, IV product content, and IV product source.

11. The method in accordance with claim 7, wherein the step of transferring comprises activating the powered delivery mechanism to insert the IV product into the docking port.

12. The method in accordance with claim 7, wherein the step of transporting comprises activating the drive mechanism of the IV product delivery device and moving the IV product delivery device.

13. The method in accordance with claim 7, further comprising the steps of:
exchanging information regarding the IV product between the IV product delivery device and the fluid delivery device; and
confirming that the fluid delivery device is an intended destination for the IV product.

14. The IV product delivery device of claim 1, wherein the powered delivery mechanism comprises a load ram movable from a first position to a second position, the load ram configured such that movement from the first position to the second position moves the at least one IV product from the IV product support into the docking port.

15. The IV product delivery device of claim 1, wherein the powered delivery mechanism comprises a robotic arm configured to engage the at least one IV product and move the at least one IV product from the IV product support into the docking port.

16. The IV product delivery device of claim 1, wherein the powered delivery mechanism is configured to tilt the IV product support and allow the at least one IV product to slide off of the IV product support into the docking port.

* * * * *